(12) United States Patent
Peng

(10) Patent No.: US 8,193,416 B1
(45) Date of Patent: Jun. 5, 2012

(54) LETTUCE VARIETY PRO GREEN 76

(75) Inventor: Yaojin Peng, Salinas, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/310,134

(22) Filed: Dec. 2, 2011

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. ........ 800/305; 435/410; 800/260; 800/278; 800/279; 800/298; 800/300; 800/301; 800/302; 800/303

(58) Field of Classification Search ........................ None
See application file for complete search history.

(56) References Cited

U.S. PATENT DOCUMENTS 6,492,579 B2 * 12/2002 Olivas et al. .................. 800/305

* cited by examiner

*Primary Examiner* — Eileen B O Hara
(74) *Attorney, Agent, or Firm* — S. Matthew Edwards

(57) ABSTRACT

A lettuce cultivar, designated Pro Green 76, is disclosed. The invention relates to the seeds of lettuce cultivar Pro Green 76, to the plants of lettuce cultivar Pro Green 76 and to methods for producing a lettuce plant by crossing the cultivar Pro Green 76 with itself or another lettuce cultivar. The invention further relates to methods for producing a lettuce plant containing in its genetic material one or more transgenes and to the transgenic lettuce plants and plant parts produced by those methods. This invention also relates to methods for producing other lettuce cultivars, lines or plant parts derived from lettuce cultivar Pro Green 76 and to the lettuce plants, varieties, and their parts derived from the use of those methods. The invention further relates to hybrid lettuce seeds, plants, and plant parts produced by crossing cultivar Pro Green 76 with another lettuce cultivar.

23 Claims, No Drawings

US 8,193,416 B1

LETTUCE VARIETY PRO GREEN 76

BACKGROUND OF THE INVENTION

The present invention relates to a leaf lettuce (*Lactuca sativa* L.) variety designated Pro Green 76. All publications cited in this application are herein incorporated by reference.

Practically speaking, all cultivated forms of lettuce belong to the highly polymorphic species *Lactuca sativa* that is grown for its edible head and leaves. *Lactuca sativa* is in the Cichoreae tribe of the Asteraceae (Compositae) family. Lettuce is related to chicory, sunflower, aster, dandelion, artichoke, and chrysanthemum. *Sativa* is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce comes in many varieties, none of which form a head, and include the green oak leaf variety. Latin lettuce looks like a cross between romaine and butterhead. Stem lettuce has long, narrow leaves and thick, edible stems. Oilseed lettuce is a type grown for its large seeds that are pressed to obtain oil. Latin lettuce, stem lettuce, and oilseed lettuce are seldom seen in the United States.

There is an ongoing need for improved lettuce varieties. Presently, there are over a thousand known lettuce cultivars. As a crop, lettuce is grown commercially wherever environmental conditions permit the production of an economically viable yield. Lettuce is the World's most popular salad.

The goal of lettuce plant breeding is to develop new, unique, and superior lettuce cultivars. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same lettuce traits. Each year, the plant breeder selects the germplasm to advance to the next generation. This germplasm is grown under different geographical, climatic, and soil conditions, and further selections are then made during, and at the end of, the growing season. The cultivars that are developed are unpredictable. A breeder of ordinary skill in the art cannot predict the final resulting lines he develops, except possibly in a very gross and general fashion. The same breeder cannot produce the same line twice by using the exact same original parents and the same selection techniques.

The development of commercial lettuce cultivars requires the development of lettuce varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable Umbelliferae," Rubatzky, V. E., et al. (1999).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Lettuce in general, and leaf lettuce in particular, is an important and valuable vegetable crop. Thus, a continuing goal of lettuce plant breeders is to develop stable, high yielding lettuce cultivars that are agronomically sound. To accomplish this goal, the lettuce breeder must select and develop lettuce plants with traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel lettuce cultivar designated Pro Green 76. This invention thus relates to the seeds of lettuce cultivar Pro Green 76, to the plants of lettuce cultivar Pro Green 76, and to methods for producing a lettuce plant produced by crossing the lettuce cultivar Pro Green 76 with itself or another lettuce plant, to methods for producing a lettuce plant containing in its genetic material one or more transgenes, and to the transgenic lettuce plants produced by that method. This invention also relates to methods for producing other lettuce cultivars derived from lettuce cultivar Pro Green 76 and to the lettuce cultivar derived by the use of those methods. This invention further relates to hybrid lettuce seeds and plants produced by crossing lettuce cultivar Pro Green 76 with another lettuce variety.

In another aspect, the present invention provides regenerable cells for use in tissue culture of lettuce cultivar Pro Green 76. The tissue culture will preferably be capable of regenerating plants having essentially all of the physiological and morphological characteristics of the foregoing lettuce plant, and of regenerating plants having substantially the same genotype as the foregoing lettuce plant. Preferably, the regenerable cells in such tissue cultures will be callus, protoplasts, meristematic cells, cotyledons, hypocotyl, leaves, pollen, embryos, roots, root tips, anthers, pistils, shoots, stems, petiole flowers, and seeds. Still further, the present invention provides lettuce plants regenerated from the tissue cultures of the invention.

Another aspect of the invention is to provide methods for producing other lettuce plants derived from lettuce cultivar Pro Green 76. Lettuce cultivars derived by the use of those methods are also part of the invention.

The invention also relates to methods for producing a lettuce plant containing in its genetic material one or more transgenes and to the transgenic lettuce plant produced by those methods.

In another aspect, the present invention provides for single gene converted plants of Pro Green 76. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring lettuce gene or a transgene introduced through genetic engineering techniques.

The invention further provides methods for developing lettuce plants in a lettuce plant breeding program using plant breeding techniques including recurrent selection, backcrossing, pedigree breeding, restriction fragment length polymorphism enhanced selection, genetic marker enhanced selection, and transformation. Seeds, lettuce plants, and parts thereof, produced by such breeding methods are also part of the invention.

In addition to the exemplary aspects and embodiments described above, further aspects and embodiments will become apparent by reference by study of the following descriptions.

DEFINITIONS

In the description and tables which follow, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Big Vein virus. Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Bolting. The premature development of a flowering stalk, and subsequent seed, before a plant produces a food crop. Bolting is typically caused by late planting when temperatures are low enough to cause vernalization of the plants.

*Bremia lactucae*. An Oomycete that causes downy mildew in lettuce in cooler growing regions.

Core length. Length of the internal lettuce stem measured from the base of the cut and trimmed head to the tip of the stem.

Corky root. A disease caused by the bacterium *Sphingomonas suberifaciens*, which causes the entire taproot to become brown, severely cracked, and non-functional.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

First water date. The date the seed first receives adequate moisture to germinate. This can and often does equal the planting date.

Gene. As used herein, "gene" refers to a segment of nucleic acid. A gene can be introduced into a genome of a species, whether from a different species or from the same species, using transformation or various breeding methods.

Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Lettuce Mosaic virus. A disease that can cause a stunted, deformed, or mottled pattern in young lettuce and yellow, twisted, and deformed leaves in older lettuce.

Maturity date. Maturity refers to the stage when the plants are of full size or optimum weight, in marketable form or shape to be of commercial or economic value.

*Nasonovia ribisnigri*. A lettuce aphid that colonizes the innermost leaves of the lettuce plant, contaminating areas that cannot be treated easily with insecticides.

Quantitative Trait Loci. Quantitative Trait Loci (QTL) refers to genetic loci that control to some degree, numerically representable traits that are usually continuously distributed.

Ratio of head height/diameter. Head height divided by the head diameter is an indication of the head shape; <1 is flattened, 1=round, and >1 is pointed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Tip burn. Means a browning of the edges or tips of lettuce leaves that is a physiological response to a lack of calcium.

Tomato Bushy Stunt. A disease which causes stunting of growth, leaf mottling, and deformed or absent fruit.

DETAILED DESCRIPTION OF THE INVENTION

Lettuce Pro Green 76 is a dark glossy green leaf lettuce variety suitable for full size production in the coastal areas of California in the Spring, Summer and Fall harvesting seasons, and the southwest deserts of California and Arizona in the winter harvesting season. Lettuce variety Pro Green 76 resulted from a cross of two green leaf lettuce varieties and subsequent numerous generations of individual plant selections chosen for their dark glossy green color and slow bolting.

The cultivar has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in cultivar Pro Green 76.

Lettuce cultivar Pro Green 76 has the following morphologic and other characteristics, described in Table 1.

Table 1

Variety Description Information

Plant:
Type: Green Leaf
Maturity date: 65 days (Summer), 95 days (winter) from first water date.
Seed:
Color: Black
Light dormancy: Light not required
Heat dormancy: Susceptible
Cotyledon (to fourth leaf stage):
Shape: Broad
Undulation: Flat
Anthocyanin distribution: Absent
Rolling: Absent
Cupping: Uncupped
Reflexing: Non
Mature Leaves:
Margin:
   Incision depth: Moderate
   Indentation: Shallowly Dentate
   Undulation of the apical margin: Strong
Hue of green color of outer leaves: Dark Green
Anthocyanin distribution: Absent
Glossiness: Glossy
Blistering: Moderate
Thickness: Intermediate
Trichomes: Absent
Plant at Market Stage
Head shape: Non-heading
Head size class: Medium
Head weight (g): 489.6
Head firmness: loose
Core:
Diameter at base of head (cm): 3.32
Core height from base of head to apex (cm): 5.83
Primary Regions of Adaptation:
  Spring area: Salinas, Imperial, San Joaquin, Calif., and Yuma, Ariz. (United States)
  Summer area: Salinas, Santa Maria, and San Benito, Calif. (United States)
  Autumn area: Yuma, Ariz., Imperial and Salinas, Calif. (United States)
  Winter area: Yuma, Ariz., Imperial and Coachella, Calif. (United States)
Disease and Stress Reactions:
Big Vein: Intermediate
Tipburn: Tolerant
Heat: Intermediate
Cold: Tolerant
Brown Rib: Resistant
Pink Rib: Resistant
Rusty Brown Discoloration: Resistant
Internal Rib Necrosis (Blackheart, Gray Rib, Gray Streak): Resistant

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed lettuce plants using transformation methods as described below to incorporate transgenes into the genetic material of the lettuce plant(s).

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Expression Vectors for Lettuce Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., *Plant Mol. Biol.*, 5:387 (1987); Teeri, et al., *EMBO J.*, 8:343 (1989); Koncz, et al., *PNAS*, 84:131 (1987); and DeBlock, et al., *EMBO J.*, 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science*, 263: 802 (1994). GFP and mutants of GFP may be used as screenable markers.

Expression Vectors for Lettuce Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in lettuce. Optionally, the inducible promoter is operably linked to a nucleotide sequence encoding a signal sequence which is operably linked to a gene for expression in lettuce. With an inducible promoter, the rate of transcription increases in response to an inducing agent.

Any inducible promoter can be used in the instant invention. See Ward, et al., *Plant Mol. Biol.*, 22:361-366 (1993). Exemplary inducible promoters include, but are not limited to, that from the ACEI system which responds to copper (Melt, et al., *PNAS*, 90:4567-4571 (1993)); In2 gene from maize which responds to benzenesulfonamide herbicide safeners (Hershey, et al., *Mol. Gen. Genet.*, 227:229-237 (1991) and Gatz, et al., *Mol. Gen. Genet.*, 243:32-38 (1994)) or Tet repressor from Tn10 (Gatz, et al., *Mol. Gen. Genet.*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS*, 88:0421 (1991).

B. Constitutive Promoters:

A constitutive promoter is operably linked to a gene for expression in lettuce or the constitutive promoter is operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell*, 2:163-171 (1990)); ubiquitin (Christensen, et al., *Plant Mol. Biol.*, 12:619-632 (1989) and Christensen, et al., *Plant Mol. Biol.*, 18:675-689 (1992)); pEMU (Last, et al., *Theor. Appl. Genet.*, 81:581-588 (1991)); MAS (Velten, et al., *EMBO J.*, 3:2723-2730 (1984)) and maize H3 histone (Lepetit, et al., *Mol. Gen. Genet.*, 231:276-285 (1992) and Atanassova, et al., *Plant J.*, 2 (3):291-300 (1992)). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT Application No. WO 96/30530.

C. Tissue-Specific or Tissue-Preferred Promoters:

A tissue-specific promoter is operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science*, 23:476-482 (1983) and Sengupta-Gopalan, et al., PNAS, 82:3320-3324 (1985)); a leaf-specific and light-induced promoter such as that from cab or rubisco (Simpson, et al., *EMBO J.*, 4(11):2723-2729 (1985) and Timko, et al., *Nature*, 318:579-582 (1985)); an anther-specific promoter such as that from LAT52 (Twell, et al., *Mol. Gen. Genet.*, 217:240-245 (1989)); a pollen-specific promoter such as that from Zm13 (Guerrero, et al., *Mol. Gen. Genet.*, 244:161-168 (1993)) or a microspore-preferred promoter such as that from apg (Twell, et al., *Sex. Plant Reprod.*, 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.*, 20:49 (1992); Close, P. S., Master's Thesis, Iowa State University (1993); Knox, C., et al., "Structure and Organization of Two Divergent Alpha-Amylase Genes from Barley," *Plant Mol. Biol.*, 9:3-17 (1987); Lerner, et al., *Plant Physiol.*, 91:124-129 (1989); Fontes, et al., *Plant Cell*, 3:483-496 (1991); Matsuoka, et al., *PNAS*, 88:834 (1991); Gould, et al., *J. Cell. Biol.*, 108:1657 (1989); Creissen, et al., *Plant J*, 2:129 (1991); Kalderon, et al., A short amino acid sequence able to specify nuclear location, *Cell*, 39:499-509 (1984); and Steifel, et al., Expression of a maize cell wall hydroxyproline-rich glycoprotein gene in early leaf and root vascular differentiation, *Plant Cell*, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.*, 114:92-6 (1981).

According to a preferred embodiment, the transgenic plant provided for commercial production of foreign protein is lettuce. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see *Methods in Plant Molecular Biology and Biotechnology*, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes that Confer Resistance to Pests or Disease and that Encode

1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., *Science*, 266:789 (1994) (cloning of the tomato Cf-9 gene for resistance to *Cladosporium fulvum*); Martin, et al., *Science*, 262:1432 (1993) (tomato Pto gene for resistance to *Pseudomonas syringae* pv. tomato encodes a protein kinase); and Mindrinos, et al., *Cell*, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

3. A lectin. See, for example, the disclosure by Van Damme, et al., *Plant Mol. Biol.*, 24:25 (1994), who disclose the nucleotide sequences of several *Clivia miniata* mannose-binding lectin genes.

4. A vitamin-binding protein such as avidin. See PCT Application No. US 93/06487, the contents of which are hereby incorporated by reference. The application teaches the use of avidin and avidin homologues as larvicides against insect pests.

5. An enzyme inhibitor, for example, a protease or proteinase inhibitor, or an amylase inhibitor. See, for example, Abe, et al., *J. Biol. Chem.*, 262:16793 (1987) (nucleotide sequence of rice cysteine proteinase inhibitor); Huub, et al., *Plant Mol. Biol.*, 21:985 (1993) (nucleotide sequence of cDNA encoding tobacco proteinase inhibitor I); and Sumitani, et al., *Biosci. Biotech. Biochem.*, 57:1243 (1993) (nucleotide sequence of *Streptomyces nitrosporeus* α-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor) and Pratt, et al., *Biochem. Biophys. Res. Comm.*, 163:1243 (1989) (an allostatin is identified in *Diploptera puntata*). See also, U.S. Pat. No. 5,266,317 to Tomalski, et al., who disclose genes encoding insect-specific, paralytic neurotoxins.

8. An insect-specific venom produced in nature, by a snake, a wasp, etc. For example, see Pang, et al, *Gene*, 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Mol. Biol.*, 23:691 (1993), who teach the nucleotide sequence of a cDNA encoding tobacco hornworm chitinase, and Kawalleck, et al., *Plant Mol. Biol.*, 21:673 (1993), who provide the nucleotide sequence of the parsley ubi4-2 polyubiquitin gene.

11. A molecule that stimulates signal transduction. For example, see the disclosure by Botella, et al., *Plant Mol. Biol.*, 24:757 (1994), of nucleotide sequences for mung bean calmodulin cDNA clones, and Griess, et al., *Plant Physiol.*, 104: 1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., *Plant Sci.*, 89:43 (1993), of heterologous expression of a cecropin-β, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., *Ann. Rev. Phytopathol.*, 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., *Nature*, 366:469 (1993), who show that transgenic plants expressing recombinant antibody genes are protected from virus attack.

17. A developmental-arrestive protein produced in nature by a pathogen or a parasite. Thus, fungal endo-α-1,4-D-polygalacturonases facilitate fungal colonization and plant nutrient released by solubilizing plant cell wall homo-α-1,4-D-galacturonase. See Lamb, et al., *Bio/technology*, 10:1436 (1992). The cloning and characterization of a gene which encodes a bean endopolygalacturonase-inhibiting protein is described by Toubart, et al., *Plant J.*, 2:367 (1992).

18. A developmental-arrestive protein produced in nature by a plant. For example, Logemann, et al., *Bio/technology*, 10:305 (1992), have shown that transgenic plants expressing the barley ribosome-inactivating gene have an increased resistance to fungal disease.

19. A lettuce mosaic potyvirus (LMV) coat protein gene introduced into *Lactuca sativa* in order to increase its resistance to LMV infection. See Dinant, et al., *Mol. Breeding*, 3:1, 75-86 (1997).

Any of the above listed disease or pest resistance genes (1-19) can be introduced into the claimed lettuce cultivar through a variety of means including but not limited to transformation and crossing.

B. Genes that Confer Resistance to an Herbicide:

Exemplary polynucleotides encoding polypeptides that confer traits desirable for herbicide resistance include acetolactate synthase (ALS) mutants that lead to herbicide resistance such as the S4 and/or Hra mutations ((resistance to herbicides including sulfonylureas, imidazolinones, triazolopyrimidines, pyrimidinyl thiobenzoates); glyphosate resistance (e.g., 5-enol-pyrovyl-shikimate-3-phosphate-synthase (EPSPS) gene, including but not limited to those described in U.S. Pat. Nos. 4,940,935, 5,188,642, 5,633,435, 6,566,587, 7,674,598 as well as all related application; or the glyphosate N-acetyltransferase (GAT) gene, described in Castle et al., *Science*, 2004, 304:1151-1154; and in U.S. Patent Application Publication Nos. 20070004912, 20050246798, and 20050060767)); glufosinate resistance (e.g, BAR; see e.g., U.S. Pat. No. 5,561,236); 2,4-D resistance (e.g. aryloxy alkanoate dioxygenase or AAD-1, AAD-12, or AAD-13), HPPD resistance (e.g. *Pseudomonas* HPPD) and PPO resistance (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone,); a cytochrome P450 or variant thereof that confers herbicide resistance or tolerance to, inter alia, HPPD-inhibitingherbicides, PPO-inhibiting herbicides and ALS-inhibiting herbicides (U.S. Patent Application Publication No. 20090011936; U.S. Pat. Nos. 6,380,465; 6,121,512; 5,349,127; 6,649,814; and 6,300,544; and PCT International Publication No. WO 2007/000077); dicamba resistance (e.g. dicamba monoxygenase), and traits desirable for processing or process products such as high oil (e.g., U.S. Pat. No. 6,232,529); modified oils (e.g., fatty acid desaturase genes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., *J. Bacteriol.*, 1988, 170:5837-5847) facilitate expression of polyhydroxyalkanoates (PHAs)); the disclosures of which are herein incorporated by reference.

Any of the above listed herbicide genes can be introduced into the claimed lettuce cultivar through a variety of means including, but not limited to, transformation and crossing.

C. Genes that Confer or Contribute to a Value-Added Trait, Such as:

1. Increased iron content of the lettuce, for example, by introducing into a plant a soybean ferritin gene as described in Goto, et al., *Acta Horticulturae.*, 521, 101-109 (2000).

2. Decreased nitrate content of leaves, for example, by introducing into a lettuce a gene coding for a nitrate reductase. See, for example, Curtis, et al., *Plant Cell Rep.*, 18:11, 889-896 (1999).

3. Increased sweetness of the lettuce by introducing a gene coding for monellin that elicits a flavor 100,000 times sweeter than sugar on a molar basis. See Penarrubia, et al., *Bio/technology*, 10:561-564 (1992).

4. Modified fatty acid metabolism, for example, by introducing into a plant an antisense gene of stearyl-ACP desaturase to increase stearic acid content of the plant. See Knultzon, et al., *PNAS*, 89:2625 (1992).

5. Modified carbohydrate composition effected, for example, by introducing into plants a gene coding for an enzyme that alters the branching pattern of starch. See Shiroza, et al., *J. Bacteria*, 170:810 (1988) (nucleotide sequence of *Streptococcus mutants* fructosyltransferase gene); Steinmetz, et al., *Mol. Gen. Genet.*, 20:220 (1985) (nucleotide sequence of *Bacillus subtilis* levansucrase gene); Pen, et al., *Bio/technology*, 10:292 (1992) (production of transgenic plants that express *Bacillus licheniformis* α-amylase); Elliot, et al., *Plant Mol. Biol.*, 21:515 (1993) (nucleotide sequences of tomato invertase genes); Søgaard, et al., *J. Biol. Chem.*, 268:22480 (1993) (site-directed mutagenesis of barley α-amylase gene); and Fisher, et al., *Plant Physiol.*, 102:1045 (1993) (maize endosperm starch branching enzyme II).

D. Genes that Control Male-Sterility:

1. Introduction of a deacetylase gene under the control of a tapetum-specific promoter and with the application of the chemical N-Ac-PPT. See International Publication WO 01/29237.

2. Introduction of various stamen-specific promoters. See International Publications WO 92/13956 and WO 92/13957.

3. Introduction of the barnase and the barstar genes. See Paul, et al., *Plant Mol. Biol.*, 19:611-622 (1992).

Methods for Lettuce Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science*, 227: 1229 (1985); Curtis, et al., *Journal of Experimental Botany*, 45:279, 1441-1449 (1994); Torres, et al., *Plant Cell Tissue and Organ Culture*, 34:3, 279-285 (1993); and Dinant, et al., *Molecular Breeding*, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.*, 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.*, 8:238 (1989). See also, U.S. Pat. No. 5,591, 616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Russell, D. R., et al., *Plant Cell Rep.*, 12 (3, Jan.), 165-169 (1993); Aragao, F. J. L., et al., *Plant Mol. Biol.*, 20 (2, Oct.), 357-359 (1992); Aragao, F. J. L., et al., *Plant Cell Rep.*, 12 (9, July), 483-490 (1993); Aragao, *Theor. Appl. Genet.*, 93:142-150 (1996); Kim, J., Minamikawa, T., *Plant Sci.*, 117:131-138 (1996); Sanford, et al., *Part. Sci. Technol.*, 5:27 (1987); Sanford, J. C., *Trends Biotech.*, 6:299 (1988); Klein, et al., *Bio/technology*, 6:559-563 (1988); Sanford, J. C., *Physiol. Plant*, 7:206 (1990); Klein, et al., *Bio/technology*, 10:268 (1992).

Another method for physical delivery of DNA to plants is sonication of target cells. Zhang, et al., *Bio/technology*, 9:996 (1991). Alternatively, liposome and spheroplast fusion have been used to introduce expression vectors into plants. Deshayes, et al., *EMBO J.*, 4:2731 (1985) and Christou, et al., *PNAS*, 84:3962 (1987). Direct uptake of DNA into protoplasts using $CaCl_2$ precipitation, polyvinyl alcohol, or poly-L-ornithine has also been reported. Hain, et al., *Mol. Gen. Genet.*, 199:161 (1985) and Draper, et al., *Plant Cell Physiol.*, 23:451 (1982). Electroporation of protoplasts and whole cells and tissues have also been described. Saker, M., Kuhne, T., *Biologia Plantarum*, 40(4):507-514 (1997/98); Donn, et al., In Abstracts of VIIth International Congress on Plant Cell and Tissue Culture IAPTC, A2-38, p. 53 (1990); D'Halluin, et al., *Plant Cell*, 4:1495-1505 (1992); and Spencer, et al., *Plant Mol. Biol.*, 24:51-61 (1994). See also Chupean, et al., *Bio/technology*, 7:5, 503-508 (1989).

Following transformation of lettuce target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic lettuce line. Alternatively, a genetic trait which has been engineered into a particular lettuce cultivar using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "lettuce plant" is used in the context of the present invention, this also includes any gene conversions of that variety. The term "gene converted plant" as used herein refers to those lettuce plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental lettuce plant which contributes the gene for the desired characteristic is termed the "nonrecurrent" or "donor parent." This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a lettuce plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Teng, et al., *HortScience*, 27:9, 1030-1032 (1992); Teng, et al., *HortScience*, 28:6, 669-1671 (1993); Zhang, et al., *Journal of Genetics and Breeding*, 46:3, 287-290 (1992); Webb, et al., *Plant Cell Tissue and Organ Culture*, 38:1, 77-79 (1994); Curtis, et al., *Journal of Experimental Botany*, 45:279, 1441-1449 (1994); Nagata, et al., *Journal for the American Society for Horticultural Science*, 125:6, 669-672 (2000); and Ibrahim, et al., *Plant Cell Tissue and Organ Culture*, 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of variety Pro Green 76.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Additional Breeding Methods

This invention also is directed to methods for producing a lettuce plant by crossing a first parent lettuce plant with a second parent lettuce plant wherein the first or second parent lettuce plant is a lettuce plant of cultivar Pro Green 76. Further, both first and second parent lettuce plants can come from lettuce cultivar Pro Green 76. Thus, any such methods using lettuce cultivar Pro Green 76 are part of this invention: selfing, backcrosses, hybrid production, crosses to populations, and the like. All plants produced using lettuce cultivar Pro Green 76 as at least one parent are within the scope of this invention, including those developed from cultivars derived from lettuce cultivar Pro Green 76. Advantageously, this lettuce cultivar could be used in crosses with other, different, lettuce plants to produce the first generation ($F_1$) lettuce hybrid seeds and plants with superior characteristics. The cultivar of the invention can also be used for transformation where exogenous genes are introduced and expressed by the cultivar of the invention. Genetic variants created either through traditional breeding methods using lettuce cultivar Pro Green 76 or through transformation of cultivar Pro Green 76 by any of a number of protocols known to those of skill in the art are intended to be within the scope of this invention.

The following describes breeding methods that may be used with lettuce cultivar Pro Green 76 in the development of further lettuce plants. One such embodiment is a method for developing cultivar Pro Green 76 progeny lettuce plants in a lettuce plant breeding program comprising: obtaining the lettuce plant, or a part thereof, of cultivar Pro Green 76, utilizing said plant or plant part as a source of breeding material, and selecting a lettuce cultivar Pro Green 76 progeny plant with molecular markers in common with cultivar Pro Green 76 and/or with morphological and/or physiological characteristics selected from the characteristics listed in Table 1. Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce cultivar Pro Green 76 progeny lettuce plants, comprising crossing cultivar Pro Green 76 with another lettuce plant, thereby producing a population of lettuce plants, which, on average, derive 50% of their alleles from lettuce cultivar Pro Green 76. A plant of this population may be selected and repeatedly selfed or sibbed with a lettuce cultivar resulting from these successive filial generations. One embodiment of this invention is the lettuce cultivar produced by this method and that has obtained at least 50% of its alleles from lettuce cultivar Pro Green 76.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes lettuce cultivar Pro Green 76 progeny lettuce plants comprising a combination of at least two cultivar Pro Green 76 traits selected from the group consisting of those listed in Table 1 or the cultivar Pro Green 76 combination of traits listed in the Summary of the Invention, so that said progeny lettuce plant is not significantly different for said traits than lettuce cultivar Pro Green 76 as determined at the 5% significance level when grown in the same environmental conditions. Using techniques described herein, molecular markers may be used to identify said progeny plant as a lettuce cultivar Pro Green 76 progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce cultivar Pro Green 76 may also be characterized through their filial relationship with lettuce cultivar Pro Green 76, as for example, being within a certain number of breeding crosses of lettuce cultivar Pro Green 76. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce cultivar Pro Green 76 and its progeny. For example, progeny produced by the methods described herein may be within 1, 2, 3, 4, or 5 breeding crosses of lettuce cultivar Pro Green 76.

As used herein, the term "plant" includes plant cells, plant protoplasts, plant cell tissue cultures from which lettuce plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

TABLES

Table 2 compares the length of the cotyledon leaf in millimeters of 20 day old seedlings of lettuce cultivar Pro Green 76 with commercial lettuce cultivars Tehema and Bergams Green and shows the ANOVA results that indicate a significant difference in the cotyledon length between the varieties at 20 days old. Data were taken in 2011 in Gilroy, Calif. on 20 plants of each variety.

TABLE 2

| Cotyledon length (mm) | | |
| --- | --- | --- |
| Pro Green 76 | Tehema | Bergams Green |
| 15 | 17 | 19 |
| 13 | 16 | 18 |
| 14 | 16 | 19 |
| 16 | 19 | 17 |
| 16 | 18 | 18 |
| 17 | 19 | 17 |
| 16 | 16 | 18 |
| 15 | 18 | 16 |
| 20 | 19 | 16 |
| 15 | 17 | 18 |
| 14 | 18 | 19 |
| 15 | 17 | 18 |
| 14 | 18 | 19 |
| 19 | 17 | 20 |
| 18 | 18 | 19 |
| 16 | 20 | 18 |
| 16 | 16 | 17 |
| 15 | 12 | 20 |
| 14 | 16 | 19 |
| 16 | 15 | 19 |

TABLE 2-continued

|  | Anova: Single Factor SUMMARY | | | | |
|---|---|---|---|---|---|
| Groups | Count | Sum | Average | Variance | |
| Pro Green 76 | 20 | 314 | 15.7 | 3.063158 | |
| Tehema | 20 | 342 | 17.1 | 3.147368 | |
| Bergams Green | 20 | 364 | 18.2 | 1.326316 | |
| ANOVA | | | | | |
| Source of Variation | SS | df | MS | F | P-value | F crit |
| Between Groups | 62.8 | 2 | 31.4 | 12.4986 | 3.16E-05 | 3.158846 |
| Within Groups | 143.2 | 57 | 2.512280702 | | | |
| Total | 206 | 59 | | | | |

Table 3 compares the width of the cotyledon leaf in millimeters of 20 day old seedlings of lettuce cultivar Pro Green 76 with commercial lettuce cultivars Tehema and Bergams Green and shows the ANOVA results that indicate a significant difference in the cotyledon width between the varieties at 20 days old. Data were taken in 2011 in Gilroy, Calif. on 20 plants of each variety.

Table 4 compares the cotyledon leaf index of 20 day old seedlings of lettuce cultivar Pro Green 76 with commercial lettuce cultivars Tehema and Bergams Green and shows the ANOVA results that indicate a significant difference in the cotyledon index between the varieties at 20 days old. Data were taken in 2011 in Gilroy, Calif. on 20 plants of each variety.

TABLE 3

| Cotyledon Width (mm) | | |
|---|---|---|
| Pro Green 76 | Tehema | Bergams Green |
| 7 | 10 | 12 |
| 9 | 11 | 12 |
| 9 | 9 | 12 |
| 9 | 11 | 11 |
| 9 | 11 | 12 |
| 15 | 12 | 11 |
| 9 | 10 | 12 |
| 9 | 10 | 11 |
| 9 | 11 | 12 |
| 7 | 9 | 12 |
| 8 | 11 | 13 |
| 9 | 10 | 12 |
| 9 | 11 | 13 |
| 9 | 11 | 11 |
| 7 | 10 | 10 |
| 7 | 11 | 11 |
| 10 | 10 | 11 |
| 8 | 9 | 12 |
| 5 | 9 | 13 |
| 10 | 10 | 13 |

|  | Anova: Single Factor SUMMARY | | | | |
|---|---|---|---|---|---|
| Groups | Count | Sum | Average | Variance | |
| Pro Green 76 | 20 | 174 | 8.7 | 3.694737 | |
| Tehema | 20 | 206 | 10.3 | 0.747368 | |
| Bergams Green | 20 | 236 | 11.8 | 0.694737 | |
| ANOVA | | | | | |
| Source of Variation | SS | df | MS | F | P-value | F crit |
| Between Groups | 96.1333333 | 2 | 48.06666667 | 28.07172 | 3.27E-09 | 3.158846 |
| Within Groups | 97.6 | 57 | 1.712280702 | | | |
| Total | 193.733333 | 59 | | | | |

TABLE 4

Cotyledon Index (calculated by dividing the cotyledon leaf length by the cotyledon leaf width)

| Pro Green 76 | Tehema | Bergams Green |
|---|---|---|
| 2.1 | 1.7 | 1.6 |
| 1.4 | 1.5 | 1.5 |
| 1.6 | 1.8 | 1.6 |
| 1.8 | 1.7 | 1.5 |
| 1.8 | 1.6 | 1.5 |
| 1.1 | 1.6 | 1.5 |
| 1.8 | 1.6 | 1.5 |
| 1.7 | 1.8 | 1.5 |
| 2.2 | 1.7 | 1.3 |
| 2.1 | 1.9 | 1.5 |
| 1.8 | 1.6 | 1.5 |
| 1.7 | 1.7 | 1.5 |
| 1.6 | 1.6 | 1.5 |
| 2.1 | 1.5 | 1.8 |
| 2.6 | 1.8 | 1.9 |
| 2.3 | 1.8 | 1.6 |
| 1.6 | 1.6 | 1.5 |
| 1.9 | 1.3 | 1.7 |
| 2.8 | 1.8 | 1.5 |
| 1.6 | 1.5 | 1.5 |

Anova: Single Factor
SUMMARY

| Groups | Count | Sum | Average | Variance |
|---|---|---|---|---|
| Pro Green 76 | 20 | 37.45675 | 1.872837302 | 0.160558 |
| Tehema | 20 | 33.24293 | 1.662146465 | 0.01889 |
| Bergams Green | 20 | 30.95828 | 1.547913753 | 0.016713 |

ANOVA

| Source of Variation | SS | df | MS | F | P-value | F crit |
|---|---|---|---|---|---|---|
| Between Groups | 1.08676702 | 2 | 0.543383512 | 8.310247 | 0.000681 | 3.158846 |
| Within Groups | 3.72706843 | 57 | 0.065387165 | | | |
| Total | 4.81383545 | 59 | | | | |

Table 5 compares the length of the $4^{th}$ true leaf measured in centimeters of 20 day old seedlings of lettuce cultivar Pro Green 76 with commercial lettuce cultivars Tehema and Bergams Green and shows the ANOVA results that indicate significant differences in the $4^{th}$ leaf length between the varieties at 20 days old. Data were taken in 2011 in Gilroy, Calif. on 20 plants of each variety.

TABLE 5

4th Leaf Length (cm)

| Pro Green 76 | Tehema | Bergams Green |
|---|---|---|
| 10.5 | 8 | 10 |
| 11.1 | 6.5 | 9.5 |
| 10.8 | 5.2 | 8.3 |
| 13.5 | 9.4 | 6.1 |
| 10.2 | 7.7 | 9.3 |
| 12.7 | 9.9 | 9.1 |
| 11.3 | 4.2 | 9 |
| 13.3 | 6.5 | 7.9 |
| 11.8 | 5.1 | 6 |
| 10.5 | 7.9 | 9.4 |
| 9.4 | 8 | 11.1 |
| 13.3 | 9.1 | 9.1 |
| 8.8 | 6.8 | 10.7 |
| 12.5 | 5.6 | 6.6 |
| 8.3 | 4.9 | 8.3 |
| 10.4 | 7.5 | 6.6 |
| 12 | 14.6 | 8.5 |
| 11.9 | 8.5 | 9.3 |

TABLE 5-continued

| 8.6 | 8.3 | 10.7 |
|---|---|---|
| 9.1 | 6.8 | 9.7 |

Anova: Single Factor
SUMMARY

| Groups | Count | Sum | Average | Variance |
|---|---|---|---|---|
| Pro Green 76 | 20 | 220 | 11 | 2.637895 |
| Tehema | 20 | 150.5 | 7.525 | 5.260921 |
| Bergams Green | 20 | 175.2 | 8.76 | 2.237263 |

ANOVA

| Source of Variation | SS | df | MS | F | P-value | F crit |
|---|---|---|---|---|---|---|
| Between Groups | 124.123 | 2 | 62.0615 | 18.36849 | 6.97E-07 | 3.158846 |
| Within Groups | 192.5855 | 57 | 3.378692982 | | | |
| Total | 316.7085 | 59 | | | | |

Table 6 compares the width of the $4^{th}$ true leaf measured in millimeters of 20 day old seedlings of leaf lettuce cultivar Pro Green 76 with commercial lettuce cultivars Tehema and Bergams Green and shows the ANOVA results that indicate significant differences in the $4^{th}$ leaf width between the varieties at 20 days old. Data were taken in 2011 in Gilroy, Calif. on 20 plants of each variety.

TABLE 6

4th Leaf Width (cm)

| Pro Green 76 | Tehema | Bergams Green |
|---|---|---|
| 5.3 | 4.2 | 5.7 |
| 5 | 3.3 | 4.5 |
| 4.5 | 2.7 | 4.5 |
| 6.1 | 4.7 | 3.3 |
| 5.3 | 3.9 | 4.5 |
| 5 | 5 | 4.5 |
| 5.5 | 2.2 | 4.1 |
| 5.4 | 3.7 | 3.9 |
| 5.3 | 2.9 | 3.1 |
| 4.6 | 3.9 | 4.7 |
| 4.5 | 4.1 | 5.3 |
| 4.8 | 4.7 | 4.5 |
| 3.8 | 4.5 | 6 |
| 5.6 | 2.8 | 3.9 |
| 3.9 | 2.6 | 4.1 |
| 4.5 | 3.2 | 3.5 |
| 5 | 6.2 | 4.1 |
| 5 | 4.2 | 5.1 |
| 3.1 | 3.6 | 4.7 |
| 4.4 | 3.5 | 5.1 |

Anova: Single Factor
SUMMARY

| Groups | Count | Sum | Average | Variance |
|---|---|---|---|---|
| Pro Green 76 | 20 | 96.6 | 4.83 | 0.486421 |
| Tehema | 20 | 75.9 | 3.795 | 0.921553 |
| Bergams Green | 20 | 89.1 | 4.455 | 0.562605 |

ANOVA

| Source of Variation | SS | df | MS | F | P-value | F crit |
|---|---|---|---|---|---|---|
| Between Groups | 10.983 | 2 | 5.4915 | 8.360233 | 0.000655 | 3.158846 |
| Within Groups | 37.441 | 57 | 0.656859649 | | | |
| Total | 48.424 | 59 | | | | |

Table 7 compares the 4$^{th}$ leaf index (calculated by dividing the 4$^{th}$ leaf length by the 4$^{th}$ leaf width) of 20 day old seedlings of lettuce cultivar Pro Green 76 with commercial lettuce cultivars Tehema and Bergams Green and shows the ANOVA results that indicate significant differences in the 4$^{th}$ leaf index between the varieties at 20 days old. Data were taken in 2011 in Gilroy, Calif. on 20 plants of each variety.

TABLE 7

4th Leaf Index

| Pro Green 76 | Tehema | Bergams Green |
|---|---|---|
| 2.0 | 1.9 | 1.8 |
| 2.2 | 2.0 | 2.1 |
| 2.4 | 1.9 | 1.8 |
| 2.2 | 2.0 | 1.8 |
| 1.9 | 2.0 | 2.1 |
| 2.5 | 2.0 | 2.0 |
| 2.1 | 1.9 | 2.2 |
| 2.5 | 1.8 | 2.0 |
| 2.2 | 1.8 | 1.9 |
| 2.3 | 2.0 | 2.0 |
| 2.1 | 2.0 | 2.1 |
| 2.8 | 1.9 | 2.0 |
| 2.3 | 1.5 | 1.8 |
| 2.2 | 2.0 | 1.7 |
| 2.1 | 1.9 | 2.0 |
| 2.3 | 2.3 | 1.9 |
| 2.4 | 2.4 | 2.1 |
| 2.4 | 2.0 | 1.8 |
| 2.8 | 2.3 | 2.3 |
| 2.1 | 1.9 | 1.9 |

Anova: Single Factor
SUMMARY

| Groups | Count | Sum | Average | Variance |
|---|---|---|---|---|
| Pro Green 76 | 20 | 45.77465 | 2.288732675 | 0.053154 |
| Tehema | 20 | 39.45878 | 1.972939015 | 0.038331 |
| Bergams Green | 20 | 39.38113 | 1.969056309 | 0.022936 |

ANOVA

| Source of Variation | SS | df | MS | F | P-value | F crit |
|---|---|---|---|---|---|---|
| Between Groups | 1.3462246 | 2 | 0.673112299 | 17.64823 | 1.08E−06 | 3.158846 |
| Within Groups | 2.17400901 | 57 | 0.038140509 | | | |
| Total | 3.52023361 | 59 | | | | |

Table 8 compares the plant weight (g) of lettuce cultivar Pro Green 76 with commercial lettuce cultivars Tehema and Bergams Green and shows the ANOVA results that indicate significant differences in the plant weight between the varieties at harvest maturity. Data were taken in 2010 and 2011 in San Juan Bautista, Calif. and Yuma, Ariz. for 20 plants of each variety.

TABLE 8

Plant Weight at Harvest Maturity

| | Trial 1 | Trial 2 | Trial 3 |
|---|---|---|---|
| Pro Green 76 | 526 | 450 | 460 |
| | 457 | 510 | 450 |
| | 470 | 440 | 480 |
| | 436 | 560 | 470 |
| | 471 | 510 | 550 |
| | 562 | 570 | 520 |
| | 415 | 580 | 550 |
| | 569 | 400 | 500 |
| | 524 | 450 | 450 |
| | 438 | 450 | 440 |

TABLE 8-continued

| | | | |
|---|---|---|---|
| | 530 | 500 | 500 |
| | 455 | 460 | 525 |
| | 471 | 450 | 530 |
| | 515 | 510 | 580 |
| | 509 | 520 | 520 |
| | 444 | 480 | 480 |
| | 527 | 450 | 480 |
| | 467 | 500 | 420 |
| | 419 | 460 | 450 |
| | 546 | 470 | 550 |
| Tehema | 488 | 410 | 510 |
| | 472 | 500 | 440 |
| | 489 | 420 | 510 |
| | 506 | 450 | 500 |
| | 596 | 540 | 530 |
| | 517 | 560 | 500 |
| | 357 | 560 | 520 |
| | 349 | 460 | 490 |
| | 528 | 540 | 580 |
| | 534 | 550 | 550 |
| | 587 | 500 | 480 |
| | 512 | 480 | 480 |
| | 487 | 560 | 580 |
| | 466 | 570 | 550 |
| | 492 | 550 | 560 |
| | 526 | 580 | 570 |
| | 536 | 570 | 490 |
| | 402 | 550 | 550 |
| | 411 | 580 | 578 |
| | 494 | 560 | 580 |
| Bergams Green | 430 | 530 | 520 |
| | 477 | 400 | 500 |
| | 460 | 540 | 480 |
| | 522 | 360 | 495 |
| | 539 | 330 | 515 |
| | 377 | 390 | 520 |
| | 504 | 270 | 515 |
| | 359 | 430 | 485 |
| | 380 | 320 | 450 |
| | 419 | 460 | 420 |
| | 522 | 430 | 480 |
| | 419 | 470 | 550 |
| | 479 | 460 | 520 |
| | 536 | 420 | 485 |
| | 458 | 390 | 500 |
| | 421 | 380 | 525 |
| | 392 | 420 | 535 |
| | 377 | 390 | 500 |
| | 368 | 450 | 525 |
| | 501 | 440 | 540 |

| Anova: Two-Factor With Replication SUMMARY | Trial 1 | Trial 2 | Trial 3 | Total |
|---|---|---|---|---|
| | | Pro Green 76 | | |
| Count | 20 | 20 | 20 | 60 |
| Sum | 9751 | 9720 | 9905 | 29376 |
| Average | 487.55 | 486 | 495.25 | 489.6 |
| Variance | 2274.47105 | 2225.263 | 1945.986842 | 2092.38 |
| | | Tehema | | |
| Count | 20 | 20 | 20 | 60 |
| Sum | 9749 | 10490 | 10548 | 30787 |
| Average | 487.45 | 524.5 | 527.4 | 513.1167 |
| Variance | 4277.10263 | 2878.684 | 1703.621053 | 3189.427 |
| | | Bergams Green | | |
| Count | 20 | 20 | 20 | 60 |
| Sum | 8940 | 8280 | 10060 | 27280 |
| Average | 447 | 414 | 503 | 454.6667 |
| Variance | 3676.10526 | 4309.474 | 958.9473684 | 4252.87 |
| | | Total | | |
| Count | 60 | 60 | 60 | |
| Sum | 28440 | 28490 | 30513 | |
| Average | 474 | 474.8333 | 508.55 | |
| Variance | 3664.33898 | 5164.379 | 1674.963559 | |

TABLE 8-continued

| ANOVA Source of Variation | SS | df | MS | F | P-value | F crit |
|---|---|---|---|---|---|---|
| Sample | 103795.478 | 2 | 51897.73889 | 19.26129 | 2.86E−08 | 3.048832 |
| Columns | 46624.2111 | 2 | 23312.10556 | 8.652038 | 0.000263 | 3.048832 |
| Interaction | 55178.2556 | 4 | 13794.56389 | 5.119705 | 0.00064 | 2.4245 |
| Within | 460743.45 | 171 | 2694.40614 | | | |
| Total | 666341.394 | 179 | | | | |

Table 9 compares the plant height (cm) of lettuce cultivar Pro Green 76 with commercial lettuce cultivars Tehema and Bergams Green and shows the ANOVA results that indicate significant differences in the plant height between the varieties at harvest maturity. Data were taken in 2010 and 2011 in San Juan Bautista, Calif. and Yuma, Ariz. for 20 plants of each variety.

TABLE 9

Plant Height (cm) at Harvest Maturity

| | Trial 1 | Trial 2 | Trial 3 |
|---|---|---|---|
| Pro Green 76 | 24 | 25 | 23 |
| | 24 | 26 | 24 |
| | 27 | 27 | 22 |
| | 26 | 28 | 25 |
| | 27 | 24 | 23 |
| | 25 | 25 | 24 |
| | 25 | 24 | 22 |
| | 26 | 25 | 22 |
| | 24 | 26 | 23 |
| | 26 | 27 | 22 |
| | 26 | 27 | 23 |
| | 24 | 26 | 24 |
| | 25 | 27 | 22 |
| | 25 | 28 | 25 |
| | 27 | 25 | 24 |
| | 24 | 27 | 22 |
| | 25 | 28 | 23 |
| | 25 | 27 | 22 |
| | 26 | 26 | 24 |
| | 25 | 28 | 23 |
| Tehema | 27 | 27 | 26 |
| | 27 | 28 | 25 |
| | 28 | 28 | 26 |
| | 26 | 29 | 26 |
| | 26 | 27 | 27 |
| | 27 | 28 | 28 |
| | 31 | 27 | 28 |
| | 29 | 29 | 27 |
| | 26 | 30 | 27 |
| | 26 | 28 | 28 |
| | 29 | 28 | 29 |
| | 27 | 27 | 28 |
| | 28 | 28 | 30 |
| | 26 | 29 | 29 |
| | 27 | 30 | 28 |
| | 28 | 28 | 29 |
| | 30 | 30 | 30 |
| | 30 | 28 | 28 |
| | 27 | 29 | 30 |
| | 27 | 28 | 28 |
| Bergams Green | 23 | 23 | 24 |
| | 25 | 22 | 25 |
| | 23 | 20 | 23 |
| | 24 | 21 | 24 |
| | 23 | 24 | 22 |
| | 25 | 23 | 25 |
| | 21 | 20 | 25 |
| | 21 | 22 | 24 |
| | 20 | 21 | 23 |
| | 23 | 22 | 25 |
| | 21 | 21 | 26 |
| | 21 | 23 | 25 |
| | 22 | 22 | 24 |

TABLE 9-continued

| | | | |
|---|---|---|---|
| | 23 | 23 | 25 |
| | 21 | 22 | 23 |
| | 24 | 22 | 24 |
| | 23 | 20 | 25 |
| | 21 | 21 | 23 |
| | 21 | 20 | 25 |
| | 22 | 21 | 24 |

Anova: Two-Factor With Replication

| SUMMARY | Trial 1 | Trial 2 | Trial 3 | Total |
|---|---|---|---|---|
| *Pro Green 76* | | | | |
| Count | 20 | 20 | 20 | 60 |
| Sum | 506 | 526 | 462 | 1494 |
| Average | 25.3 | 26.3 | 23.1 | 24.9 |
| Variance | 1.06315789 | 1.694737 | 1.042105263 | 3.040678 |
| *Tehema* | | | | |
| Count | 20 | 20 | 20 | 60 |
| Sum | 552 | 566 | 557 | 1675 |
| Average | 27.6 | 28.3 | 27.85 | 27.91667 |
| Variance | 2.25263158 | 0.957895 | 2.028947368 | 1.772599 |
| *Bergams Green* | | | | |
| Count | 20 | 20 | 20 | 60 |
| Sum | 447 | 433 | 484 | 1364 |
| Average | 22.35 | 21.65 | 24.2 | 22.73333 |
| Variance | 2.13421053 | 1.397368 | 1.010526316 | 2.639548 |
| *Total* | | | | |
| Count | 60 | 60 | 60 | |
| Sum | 1505 | 1525 | 1503 | |
| Average | 25.0833333 | 25.41667 | 25.05 | |
| Variance | 6.45056497 | 9.196328 | 5.505932203 | |

ANOVA

| Source of Variation | SS | df | MS | F | P-value | F crit |
|---|---|---|---|---|---|---|
| Sample | 813.233333 | 2 | 406.6166667 | 269.4495 | 1.39E−53 | 3.048832 |
| Columns | 4.93333333 | 2 | 2.466666667 | 1.634567 | 0.198069 | 3.048832 |
| Interaction | 176.733333 | 4 | 44.18333333 | 29.27863 | 1.52E−18 | 2.4245 |
| Within | 258.05 | 171 | 1.509064327 | | | |
| Total | 1252.95 | 179 | | | | |

Table 10 compares the frame leaf length (cm) of lettuce cultivar Pro Green 76 with commercial lettuce cultivars Tehema and Bergams Green and shows the ANOVA results that indicate significant differences in frame leaf length between the varieties at harvest maturity. Data were taken in 2010 and 2011 in San Juan Bautista, Calif. and Yuma, Ariz. for 20 plants of each variety.

TABLE 10

| | Frame Leaf Length (cm) at Harvest Maturity | | |
|---|---|---|---|
| | Trial 1 | Trial 2 | Trial 3 |
| Pro Green 76 | 23 | 24 | 24 |
| | 24 | 25 | 22 |
| | 26 | 24 | 21 |
| | 25 | 24 | 22 |
| | 26 | 25 | 20 |
| | 25 | 24 | 23 |
| | 25 | 25 | 24 |
| | 26 | 25 | 22 |
| | 24 | 23 | 25 |
| | 25 | 26 | 26 |
| | 26 | 25 | 25 |
| | 24 | 25 | 22 |
| | 24 | 26 | 21 |
| | 25 | 25 | 22 |
| | 27 | 24 | 23 |
| | 23 | 25 | 24 |

TABLE 10-continued

| | | | |
|---|---|---|---|
| | 24 | 26 | 23 |
| | 25 | 26 | 24 |
| | 26 | 27 | 27 |
| | 24 | 26 | 22 |
| Tehema | 27 | 26 | 24 |
| | 25 | 26 | 24 |
| | 27 | 27 | 24 |
| | 26 | 26 | 24 |
| | 26 | 27 | 24 |
| | 26 | 26 | 25 |
| | 30 | 26 | 25 |
| | 28 | 27 | 24 |
| | 25 | 27 | 24 |
| | 26 | 26 | 25 |
| | 28 | 25 | 25 |
| | 26 | 27 | 24 |
| | 27 | 26 | 26 |
| | 25 | 27 | 26 |
| | 27 | 26 | 25 |
| | 28 | 27 | 26 |
| | 28 | 28 | 26 |
| | 29 | 27 | 25 |
| | 27 | 26 | 26 |
| | 27 | 26 | 24 |
| Bergams Green | 23 | 21 | 23 |
| | 24 | 22 | 24 |
| | 23 | 20 | 20 |
| | 24 | 20 | 23 |
| | 22 | 23 | 24 |
| | 25 | 21 | 22 |
| | 21 | 20 | 21 |
| | 21 | 21 | 25 |
| | 20 | 20 | 26 |
| | 22 | 21 | 25 |
| | 20 | 21 | 22 |
| | 21 | 22 | 23 |
| | 21 | 21 | 23 |
| | 22 | 22 | 25 |
| | 19 | 21 | 27 |
| | 23 | 20 | 26 |
| | 22 | 21 | 23 |
| | 20 | 20 | 24 |
| | 21 | 21 | 23 |
| | 21 | 21 | 23 |

Anova: Two-Factor With Replication

| SUMMARY | Trial 1 | Trial 2 | Trial 3 | Total |
|---|---|---|---|---|
| | | Pro Green 76 | | |
| Count | 20 | 20 | 20 | 60 |
| Sum | 497 | 500 | 462 | 1459 |
| Average | 24.85 | 25 | 23.1 | 24.31667 |
| Variance | 1.18684211 | 0.947368 | 3.147368421 | 2.457345 |
| | | Tehema | | |
| Count | 20 | 20 | 20 | 60 |
| Sum | 538 | 529 | 496 | 1563 |
| Average | 26.9 | 26.45 | 24.8 | 26.05 |
| Variance | 1.77894737 | 0.471053 | 0.694736842 | 1.777119 |
| | | Bergams Green | | |
| Count | 20 | 20 | 20 | 60 |
| Sum | 435 | 419 | 472 | 1326 |
| Average | 21.75 | 20.95 | 23.6 | 22.1 |
| Variance | 2.40789474 | 0.681579 | 2.989473684 | 3.210169 |
| | | Total | | |
| Count | 60 | 60 | 60 | |
| Sum | 1470 | 1448 | 1430 | |
| Average | 24.5 | 24.13333 | 23.83333333 | |
| Variance | 6.28813559 | 6.185311 | 2.717514124 | |

ANOVA

| Source of Variation | SS | df | MS | F | P-value | F crit |
|---|---|---|---|---|---|---|
| Sample | 470.411111 | 2 | 235.2055556 | 147.977 | 4.99E−38 | 3.048832 |
| Columns | 13.3777778 | 2 | 6.688888889 | 4.208241 | 0.016441 | 3.048832 |
| Interaction | 154.055556 | 4 | 38.51388889 | 24.23059 | 6.77E−16 | 2.4245 |

TABLE 10-continued

| | | | |
|---|---|---|---|
| Within | 271.8 | 171 | 1.589473684 |
| Total | 909.644444 | 179 | |

Table 11 compares the frame leaf width (cm) of lettuce cultivar Pro Green 76 with commercial lettuce cultivars Tehema and Bergams Green and shows the ANOVA results that indicate significant differences in frame leaf width between the varieties at harvest maturity. Data were taken in 2010 and 2011 in San Juan Bautista, Calif. and Yuma, Ariz. for 20 plants of each variety.

TABLE 11

Frame Leaf Width (cm) at Harvest Maturity

| | Trial 1 | Trial 2 | Trial 3 |
|---|---|---|---|
| Pro Green 76 | 22 | 20 | 22 |
| | 22 | 24 | 20 |
| | 24 | 20 | 20 |
| | 23 | 22 | 20 |
| | 23 | 22 | 18 |
| | 21 | 20 | 22 |
| | 23 | 24 | 20 |
| | 22 | 24 | 20 |
| | 25 | 22 | 23 |
| | 22 | 22 | 23 |
| | 22 | 20 | 22 |
| | 23 | 20 | 20 |
| | 22 | 24 | 19 |
| | 22 | 24 | 20 |
| | 24 | 20 | 20 |
| | 21 | 20 | 20 |
| | 22 | 22 | 20 |
| | 23 | 20 | 20 |
| | 23 | 23 | 24 |
| | 22 | 22 | 20 |
| Tehema | 24 | 23 | 20 |
| | 24 | 26 | 21 |
| | 23 | 24 | 21 |
| | 22 | 25 | 20 |
| | 22 | 26 | 21 |
| | 23 | 25 | 21 |
| | 27 | 26 | 21 |
| | 24 | 26 | 20 |
| | 21 | 25 | 21 |
| | 26 | 24 | 21 |
| | 24 | 23 | 21 |
| | 22 | 26 | 20 |
| | 22 | 25 | 22 |
| | 22 | 26 | 22 |
| | 23 | 26 | 23 |
| | 24 | 26 | 21 |
| | 23 | 27 | 21 |
| | 24 | 27 | 20 |
| | 23 | 25 | 20 |
| | 23 | 26 | 20 |
| Bergams Green | 21 | 20 | 21 |
| | 23 | 21 | 22 |
| | 22 | 20 | 19 |
| | 23 | 19 | 21 |
| | 22 | 21 | 22 |
| | 22 | 20 | 20 |
| | 19 | 19 | 20 |
| | 21 | 20 | 22 |
| | 21 | 20 | 23 |
| | 22 | 20 | 22 |
| | 20 | 20 | 20 |
| | 19 | 20 | 20 |
| | 20 | 19 | 20 |
| | 21 | 20 | 22 |
| | 19 | 20 | 24 |
| | 22 | 19 | 22 |
| | 20 | 20 | 20 |
| | 19 | 19 | 20 |
| | 18 | 20 | 20 |

TABLE 11-continued

|  | 21 | 20 | 20 |
|---|---|---|---|
| Anova: Two-Factor With Replication SUMMARY | Trial 1 | Trial 2 | Trial 3 | Total |

| Pro Green 76 | | | | |
|---|---|---|---|---|
| Count | 20 | 20 | 20 | 60 |
| Sum | 451 | 435 | 413 | 1299 |
| Average | 22.55 | 21.75 | 20.65 | 21.65 |
| Variance | 0.99736842 | 2.723684 | 2.239473684 | 2.536441 |

| Tehema | | | | |
|---|---|---|---|---|
| Count | 20 | 20 | 20 | 60 |
| Sum | 466 | 507 | 417 | 1390 |
| Average | 23.3 | 25.35 | 20.85 | 23.16667 |
| Variance | 2.01052632 | 1.292105 | 0.660526316 | 4.717514 |

| Bergams Green | | | | |
|---|---|---|---|---|
| Count | 20 | 20 | 20 | 60 |
| Sum | 415 | 397 | 420 | 1232 |
| Average | 20.75 | 19.85 | 21 | 20.53333 |
| Variance | 2.09210526 | 0.344737 | 1.684210526 | 1.575141 |

| Total | | | | |
|---|---|---|---|---|
| Count | 60 | 60 | 60 | |
| Sum | 1332 | 1339 | 1250 | |
| Average | 22.2 | 22.31667 | 20.83333333 | |
| Variance | 2.80677966 | 6.694633 | 1.497175141 | |

| ANOVA | | | | | | |
|---|---|---|---|---|---|---|
| Source of Variation | SS | df | MS | F | P-value | F crit |
| Sample | 209.633333 | 2 | 104.8166667 | 67.16751 | 2.97E−22 | 3.048832 |
| Columns | 81.6333333 | 2 | 40.81666667 | 26.15571 | 1.23E−10 | 3.048832 |
| Interaction | 172.433333 | 4 | 43.10833333 | 27.62423 | 1.07E−17 | 2.4245 |
| Within | 266.85 | 171 | 1.560526316 | | | |
| Total | 730.55 | 179 | | | | |

Table 12 compares the frame leaf index of lettuce cultivar Pro Green 76 with commercial lettuce cultivars Tehema and Bergams Green and shows the ANOVA results that indicate significant differences in frame leaf index between the varieties at harvest maturity. Data were taken in 2010 and 2011 in San Juan Bautista, Calif. and Yuma, Ariz. for 20 plants of each variety.

TABLE 12

| Frame Leaf Index at Harvest Mature (calculated by dividing the leaf length by the leaf width) | | | |
|---|---|---|---|
| | Trial 1 | Trial 2 | Trial 3 |
| Pro Green 76 | 1.05 | 1.20 | 1.09 |
| | 1.09 | 1.04 | 1.10 |
| | 1.08 | 1.20 | 1.05 |
| | 1.09 | 1.09 | 1.10 |
| | 1.13 | 1.14 | 1.11 |
| | 1.19 | 1.20 | 1.05 |
| | 1.09 | 1.04 | 1.20 |
| | 1.18 | 1.04 | 1.10 |
| | 0.96 | 1.05 | 1.09 |
| | 1.14 | 1.18 | 1.13 |
| | 1.18 | 1.25 | 1.14 |
| | 1.04 | 1.25 | 1.10 |
| | 1.09 | 1.08 | 1.11 |
| | 1.14 | 1.04 | 1.10 |
| | 1.13 | 1.20 | 1.15 |
| | 1.10 | 1.25 | 1.20 |
| | 1.09 | 1.18 | 1.15 |
| | 1.09 | 1.30 | 1.20 |
| | 1.13 | 1.17 | 1.13 |
| | 1.09 | 1.18 | 1.10 |
| Tehema | 1.13 | 1.13 | 1.20 |
| | 1.04 | 1.00 | 1.14 |

TABLE 12-continued

|  |  |  |  |
|---|---|---|---|
|  | 1.17 | 1.13 | 1.14 |
|  | 1.18 | 1.04 | 1.20 |
|  | 1.18 | 1.04 | 1.14 |
|  | 1.13 | 1.04 | 1.19 |
|  | 1.11 | 1.00 | 1.19 |
|  | 1.17 | 1.04 | 1.20 |
|  | 1.19 | 1.08 | 1.14 |
|  | 1.00 | 1.08 | 1.19 |
|  | 1.17 | 1.09 | 1.19 |
|  | 1.18 | 1.04 | 1.20 |
|  | 1.23 | 1.04 | 1.18 |
|  | 1.14 | 1.04 | 1.18 |
|  | 1.17 | 1.00 | 1.09 |
|  | 1.17 | 1.04 | 1.24 |
|  | 1.22 | 1.04 | 1.24 |
|  | 1.21 | 1.00 | 1.25 |
|  | 1.17 | 1.04 | 1.30 |
|  | 1.17 | 1.00 | 1.20 |
| Bergams Green | 1.10 | 1.05 | 1.10 |
|  | 1.04 | 1.05 | 1.09 |
|  | 1.05 | 1.00 | 1.05 |
|  | 1.04 | 1.05 | 1.10 |
|  | 1.00 | 1.10 | 1.09 |
|  | 1.14 | 1.05 | 1.10 |
|  | 1.11 | 1.05 | 1.05 |
|  | 1.00 | 1.05 | 1.14 |
|  | 0.95 | 1.00 | 1.13 |
|  | 1.00 | 1.05 | 1.14 |
|  | 1.00 | 1.05 | 1.10 |
|  | 1.11 | 1.10 | 1.15 |
|  | 1.05 | 1.11 | 1.15 |
|  | 1.05 | 1.10 | 1.14 |
|  | 1.00 | 1.05 | 1.13 |
|  | 1.05 | 1.05 | 1.18 |
|  | 1.10 | 1.05 | 1.15 |
|  | 1.05 | 1.05 | 1.20 |
|  | 1.17 | 1.05 | 1.15 |
|  | 1.00 | 1.05 | 1.15 |

Anova: Two-Factor With Replication

| SUMMARY | Trial 1 | Trial 2 | Trial 3 | Total |
|---|---|---|---|---|
| | | Pro Green 76 | | |
| Count | 20 | 20 | 20 | 60 |
| Sum | 22.0647196 | 23.09209 | 22.38149285 | 67.53831 |
| Average | 1.10323598 | 1.154605 | 1.119074642 | 1.125638 |
| Variance | 0.00281045 | 0.006931 | 0.001919784 | 0.004224 |
| | | Tehema | | |
| Count | 20 | 20 | 20 | 60 |
| Sum | 23.1291565 | 20.89507 | 23.81011669 | 67.83434 |
| Average | 1.15645782 | 1.044753 | 1.190505835 | 1.130572 |
| Variance | 0.00304315 | 0.001508 | 0.00212967 | 0.006093 |
| | | Bergams Green | | |
| Count | 20 | 20 | 20 | 60 |
| Sum | 20.9892919 | 21.10865 | 22.47126982 | 64.56921 |
| Average | 1.0494646 | 1.055432 | 1.123563491 | 1.076153 |
| Variance | 0.00296774 | 0.000765 | 0.001503267 | 0.002835 |
| | | Total | | |
| Count | 60 | 60 | 60 | |
| Sum | 66.1831679 | 65.09581 | 68.66287937 | |
| Average | 1.1030528 | 1.08493 | 1.144381323 | |
| Variance | 0.00478105 | 0.005452 | 0.002873344 | |

ANOVA

| Source of Variation | SS | df | MS | F | P-value | F crit |
|---|---|---|---|---|---|---|
| Sample | 0.10869048 | 2 | 0.05434524 | 20.744 | 8.59E−09 | 3.048832 |
| Columns | 0.11141829 | 2 | 0.055709145 | 21.26461 | 5.66E−09 | 3.048832 |
| Interaction | 0.21658837 | 4 | 0.054147093 | 20.66836 | 6.55E−14 | 2.4245 |
| Within | 0.44798675 | 171 | 0.002619806 | | | |
| Total | 0.88468389 | 179 | | | | |

Table 13 compares the frame leaf area (cm2, calculated by multiplying the leaf length by the leaf width) of lettuce cultivar Pro Green 76 with commercial lettuce cultivars Tehema and Bergams Green and shows the ANOVA results that indicate significant differences in the frame leaf area between the varieties at harvest maturity. Data were taken in 2010 and 2011 in San Juan Bautista, Calif. and Yuma, Ariz. for 20 plants of each variety.

TABLE 13

| | Leaf Area (cm2, calculated by multiplying the leaf length by the leaf width) | | |
|---|---|---|---|
| | Trial 1 | Trial 2 | Trial 3 |
| Pro Green 76 | 506.00 | 480.00 | 528.00 |
| | 528.00 | 600.00 | 440.00 |
| | 624.00 | 480.00 | 420.00 |
| | 575.00 | 528.00 | 440.00 |
| | 598.00 | 550.00 | 360.00 |
| | 525.00 | 480.00 | 506.00 |
| | 575.00 | 600.00 | 480.00 |
| | 572.00 | 600.00 | 440.00 |
| | 600.00 | 506.00 | 575.00 |
| | 550.00 | 572.00 | 598.00 |
| | 572.00 | 500.00 | 550.00 |
| | 552.00 | 500.00 | 440.00 |
| | 528.00 | 624.00 | 399.00 |
| | 550.00 | 600.00 | 440.00 |
| | 648.00 | 480.00 | 460.00 |
| | 483.00 | 500.00 | 480.00 |
| | 528.00 | 572.00 | 460.00 |
| | 575.00 | 520.00 | 480.00 |
| | 598.00 | 621.00 | 648.00 |
| | 528.00 | 572.00 | 440.00 |
| Tehema | 648.00 | 598.00 | 480.00 |
| | 600.00 | 676.00 | 504.00 |
| | 621.00 | 648.00 | 504.00 |
| | 572.00 | 650.00 | 480.00 |
| | 572.00 | 702.00 | 504.00 |
| | 598.00 | 650.00 | 525.00 |
| | 810.00 | 676.00 | 525.00 |
| | 672.00 | 702.00 | 480.00 |
| | 525.00 | 675.00 | 504.00 |
| | 676.00 | 624.00 | 525.00 |
| | 672.00 | 575.00 | 525.00 |
| | 572.00 | 702.00 | 480.00 |
| | 594.00 | 650.00 | 572.00 |
| | 550.00 | 702.00 | 572.00 |
| | 621.00 | 676.00 | 575.00 |
| | 672.00 | 702.00 | 546.00 |
| | 644.00 | 756.00 | 546.00 |
| | 696.00 | 729.00 | 500.00 |
| | 621.00 | 650.00 | 520.00 |
| | 621.00 | 676.00 | 480.00 |
| Bergams Green | 483.00 | 420.00 | 483.00 |
| | 552.00 | 462.00 | 528.00 |
| | 506.00 | 400.00 | 380.00 |
| | 552.00 | 380.00 | 483.00 |
| | 484.00 | 483.00 | 528.00 |
| | 550.00 | 420.00 | 440.00 |
| | 399.00 | 380.00 | 420.00 |
| | 441.00 | 420.00 | 550.00 |
| | 420.00 | 400.00 | 598.00 |
| | 484.00 | 420.00 | 550.00 |
| | 400.00 | 420.00 | 440.00 |
| | 399.00 | 440.00 | 460.00 |
| | 420.00 | 399.00 | 460.00 |
| | 462.00 | 440.00 | 550.00 |
| | 361.00 | 420.00 | 648.00 |
| | 506.00 | 380.00 | 572.00 |
| | 440.00 | 420.00 | 460.00 |
| | 380.00 | 380.00 | 480.00 |
| | 378.00 | 420.00 | 460.00 |
| | 441.00 | 420.00 | 460.00 |

TABLE 13-continued

| Anova: Two-Factor With Replication SUMMARY | Trial 1 | Trial 2 | Trial 3 | Total |
|---|---|---|---|---|
| Pro Green 76 | | | | |
| Count | 20 | 20 | 20 | 60 |
| Sum | 11215 | 10885 | 9584 | 31684 |
| Average | 560.75 | 544.25 | 479.2 | 528.0667 |
| Variance | 1668.93421 | 2722.513 | 4947.431579 | 4267.792 |
| Tehema | | | | |
| Count | 20 | 20 | 20 | 60 |
| Sum | 12557 | 13419 | 10347 | 36323 |
| Average | 627.85 | 670.95 | 517.35 | 605.3833 |
| Variance | 3981.71316 | 1818.787 | 1008.871053 | 6448.308 |
| Bergams Green | | | | |
| Count | 20 | 20 | 20 | 60 |
| Sum | 9058 | 8324 | 9950 | 27332 |
| Average | 452.9 | 416.2 | 497.5 | 455.5333 |
| Variance | 3590.83158 | 730.8 | 4348.052632 | 3915.745 |
| Total | | | | |
| Count | 60 | 60 | 60 | |
| Sum | 32830 | 32628 | 29881 | |
| Average | 547.166667 | 543.8 | 498.0166667 | |
| Variance | 8257.59887 | 12697.48 | 3565.169209 | |

ANOVA

| Source of Variation | SS | df | MS | F | P-value | F crit |
|---|---|---|---|---|---|---|
| Sample | 673879.478 | 2 | 336939.7389 | 122.1882 | 1.11E−33 | 3.048832 |
| Columns | 90463.4111 | 2 | 45231.70556 | 16.40287 | 3.04E−07 | 3.048832 |
| Interaction | 301274.689 | 4 | 75318.67222 | 27.31364 | 1.55E−17 | 2.4245 |
| Within | 471540.75 | 171 | 2757.548246 | | | |
| Total | 1537158.33 | 179 | | | | |

Table 14 compares the core length (mm) of lettuce cultivar Pro Green 76 with commercial lettuce cultivars Tehema and Bergams Green and shows the ANOVA results that indicate significant differences in the core length between the varieties at harvest maturity. Data were taken in 2010 and 2011 in San Juan Bautista, Calif. and Yuma, Ariz. for 20 plants of each variety.

TABLE 14

| Core Length (mm) at Harvest Maturity | | | |
|---|---|---|---|
| | Trial 1 | Trial 2 | Trial 3 |
| Pro Green 76 | 41 | 65 | 65 |
| | 41 | 62 | 60 |
| | 53 | 75 | 55 |
| | 58 | 60 | 55 |
| | 40 | 75 | 56 |
| | 44 | 65 | 65 |
| | 41 | 65 | 65 |
| | 41 | 65 | 68 |
| | 58 | 70 | 58 |
| | 59 | 70 | 60 |
| | 43 | 75 | 68 |
| | 50 | 70 | 52 |
| | 57 | 65 | 56 |
| | 40 | 66 | 58 |
| | 51 | 65 | 56 |
| | 43 | 66 | 55 |
| | 58 | 67 | 58 |
| | 61 | 67 | 55 |
| | 46 | 65 | 65 |
| | 40 | 60 | 62 |
| Tehema | 39 | 65 | 40 |
| | 45 | 60 | 42 |
| | 32 | 65 | 41 |
| | 53 | 62 | 38 |

TABLE 14-continued

| | | | |
|---|---|---|---|
| | 41 | 65 | 42 |
| | 52 | 66 | 35 |
| | 38 | 62 | 42 |
| | 38 | 65 | 42 |
| | 52 | 65 | 40 |
| | 51 | 64 | 42 |
| | 53 | 60 | 40 |
| | 51 | 60 | 38 |
| | 36 | 65 | 39 |
| | 38 | 66 | 41 |
| | 44 | 65 | 42 |
| | 47 | 64 | 41 |
| | 30 | 64 | 42 |
| | 37 | 60 | 41 |
| | 40 | 59 | 39 |
| | 46 | 61 | 42 |
| Bergams Green | 32 | 68 | 50 |
| | 35 | 70 | 60 |
| | 36 | 70 | 55 |
| | 38 | 70 | 65 |
| | 36 | 72 | 65 |
| | 35 | 70 | 55 |
| | 33 | 70 | 50 |
| | 36 | 68 | 50 |
| | 33 | 68 | 56 |
| | 31 | 65 | 65 |
| | 39 | 72 | 68 |
| | 37 | 72 | 55 |
| | 46 | 70 | 50 |
| | 30 | 69 | 52 |
| | 36 | 70 | 55 |
| | 36 | 70 | 56 |
| | 38 | 72 | 60 |
| | 41 | 68 | 65 |
| | 41 | 75 | 68 |
| | 34 | 70 | 65 |

Anova: Two-Factor With Replication

| SUMMARY | Trial 1 | Trial 2 | Trial 3 | Total |
|---|---|---|---|---|
| | | Pro Green 76 | | |
| Count | 20 | 20 | 20 | 60 |
| Sum | 965 | 1338 | 1192 | 3495 |
| Average | 48.25 | 66.9 | 59.6 | 58.25 |
| Variance | 61.3552632 | 19.56842 | 23.83157895 | 93.61441 |
| | | Tehema | | |
| Count | 20 | 20 | 20 | 60 |
| Sum | 863 | 1263 | 809 | 2935 |
| Average | 43.15 | 63.15 | 40.45 | 48.91667 |
| Variance | 52.5552632 | 5.607895 | 3.523684211 | 124.1116 |
| | | Bergams Green | | |
| Count | 20 | 20 | 20 | 60 |
| Sum | 723 | 1399 | 1165 | 3287 |
| Average | 36.15 | 69.95 | 58.25 | 54.78333 |
| Variance | 14.1342105 | 4.365789 | 41.46052632 | 219.054 |
| | | Total | | |
| Count | 60 | 60 | 60 | |
| Sum | 2551 | 4000 | 3166 | |
| Average | 42.5166667 | 66.66667 | 52.76666667 | |
| Variance | 66.2539548 | 17.37853 | 99.60564972 | |

ANOVA

| Source of Variation | SS | df | MS | F | P-value | F crit |
|---|---|---|---|---|---|---|
| Sample | 2670.93333 | 2 | 1335.466667 | 53.08772 | 1.16E−18 | 3.048832 |
| Columns | 17629.9 | 2 | 8814.95 | 350.4136 | 3.27E−61 | 3.048832 |
| Interaction | 3838.46667 | 4 | 959.6166667 | 38.14686 | 8.57E−23 | 2.4245 |
| Within | 4301.65 | 171 | 25.15584795 | | | |
| Total | 28440.95 | 179 | | | | |

Table 15 compares the diameter length (mm) of lettuce cultivar Pro Green 76 with commercial lettuce cultivars Tehema and Bergams Green and shows the ANOVA results that indicate non significant differences in the core diameter between the varieties at harvest maturity. Data were taken in 2010 and 2011 in San Juan Bautista, Calif. and Yuma, Ariz. for 20 plants of each variety.

TABLE 15

Core Diameter (mm) at Harvest Maturity

| | Trial 1 | Trial 2 | Trial 3 |
|---|---|---|---|
| Pro Green 76 | 31 | 35 | 36 |
| | 34 | 35 | 35 |
| | 35 | 32 | 30 |
| | 39 | 32 | 30 |
| | 34 | 32 | 30 |
| | 35 | 35 | 35 |
| | 32 | 32 | 30 |
| | 37 | 35 | 32 |
| | 35 | 32 | 30 |
| | 37 | 35 | 30 |
| | 34 | 32 | 36 |
| | 35 | 35 | 29 |
| | 32 | 32 | 30 |
| | 35 | 32 | 32 |
| | 32 | 35 | 32 |
| | 35 | 32 | 30 |
| | 32 | 34 | 32 |
| | 39 | 32 | 30 |
| | 34 | 35 | 34 |
| | 34 | 30 | 32 |
| Tehema | 38 | 38 | 30 |
| | 37 | 35 | 30 |
| | 34 | 34 | 30 |
| | 36 | 34 | 28 |
| | 39 | 35 | 30 |
| | 34 | 35 | 25 |
| | 35 | 34 | 30 |
| | 34 | 35 | 31 |
| | 36 | 35 | 29 |
| | 39 | 34 | 30 |
| | 36 | 33 | 30 |
| | 39 | 32 | 28 |
| | 35 | 35 | 28 |
| | 34 | 35 | 29 |
| | 38 | 34 | 30 |
| | 35 | 35 | 30 |
| | 34 | 35 | 30 |
| | 36 | 32 | 30 |
| | 38 | 31 | 29 |
| | 37 | 32 | 30 |
| Bergams Green | 39 | 30 | 30 |
| | 38 | 35 | 35 |
| | 36 | 30 | 30 |
| | 36 | 30 | 32 |
| | 36 | 30 | 35 |
| | 33 | 35 | 30 |
| | 38 | 35 | 30 |
| | 38 | 30 | 30 |
| | 34 | 30 | 35 |
| | 37 | 30 | 35 |
| | 37 | 30 | 36 |
| | 35 | 35 | 35 |
| | 36 | 35 | 30 |
| | 35 | 32 | 30 |
| | 34 | 33 | 30 |
| | 33 | 32 | 30 |
| | 34 | 32 | 35 |
| | 36 | 30 | 35 |
| | 34 | 35 | 36 |
| | 36 | 30 | 35 |

TABLE 15-continued

| Anova: Two-Factor With Replication SUMMARY | Trial 1 | Trial 2 | Trial 3 | Total |
|---|---|---|---|---|
| Pro Green 76 | | | | |
| Count | 20 | 20 | 20 | 60 |
| Sum | 691 | 664 | 635 | 1990 |
| Average | 34.55 | 33.2 | 31.75 | 33.16667 |
| Variance | 4.89210526 | 2.694737 | 5.144736842 | 5.429379 |
| Tehema | | | | |
| Count | 20 | 20 | 20 | 60 |
| Sum | 724 | 683 | 587 | 1994 |
| Average | 36.2 | 34.15 | 29.35 | 33.23333 |
| Variance | 3.32631579 | 2.45 | 1.713157895 | 10.79209 |
| Bergams Green | | | | |
| Count | 20 | 20 | 20 | 60 |
| Sum | 715 | 639 | 654 | 2008 |
| Average | 35.75 | 31.95 | 32.7 | 33.46667 |
| Variance | 3.03947368 | 4.997368 | 6.852631579 | 7.541243 |
| Total | | | | |
| Count | 60 | 60 | 60 | |
| Sum | 2130 | 1986 | 1876 | |
| Average | 35.5 | 33.1 | 31.26666667 | |
| Variance | 4.11864407 | 4.091525 | 6.436158192 | |

ANOVA

| Source of Variation | SS | df | MS | F | P-value | F crit |
|---|---|---|---|---|---|---|
| Sample | 2.97777778 | 2 | 1.488888889 | 0.381652 | 0.683313 | 3.048832 |
| Columns | 540.844444 | 2 | 270.4222222 | 69.31824 | 8.98E−23 | 3.048832 |
| Interaction | 194.055556 | 4 | 48.51388889 | 12.43573 | 6.69E−09 | 2.4245 |
| Within | 667.1 | 171 | 3.901169591 | | | |
| Total | 1404.97778 | 179 | | | | |

Table 16 compares the seed stalk height measured in centimeters of lettuce cultivar Pro Green 76 with commercial lettuce cultivars Tehema and Bergams and shows the ANOVA results that indicate significant differences in the seed stalk height between the varieties. Data were taken in 2011 in Bottonwillow, Calif. on 20 plants of each variety.

TABLE 16

| Seed Stalk Height (cm) | | |
|---|---|---|
| Pro Green 76 | Tehema | Bergams Green |
| 110 | 91 | 95 |
| 105 | 104 | 90 |
| 120 | 95 | 101 |
| 110 | 90 | 105 |
| 105 | 85 | 90 |
| 99 | 89 | 95 |
| 100 | 102 | 96 |
| 110 | 105 | 88 |
| 115 | 100 | 89 |
| 110 | 95 | 90 |
| 100 | 90 | 92 |
| 95 | 95 | 91 |
| 120 | 92 | 90 |
| 110 | 90 | 100 |
| 105 | 88 | 105 |
| 110 | 89 | 11 |
| 112 | 100 | 106 |
| 115 | 105 | 105 |
| 120 | 100 | 95 |
| 110 | 98 | 90 |

TABLE 16-continued

Anova: Single Factor

SUMMARY

| Groups | Count | Sum | Average | Variance |
|---|---|---|---|---|
| Preogreen 76 | 20 | 2181 | 109.05 | 50.36579 |
| Tehema | 20 | 1903 | 95.15 | 38.66053 |
| Bergams Green | 20 | 1824 | 91.2 | 393.9579 |

ANOVA

| Source of Variation | SS | df | MS | F | P-value | F crit |
|---|---|---|---|---|---|---|
| Between Groups | 3516.23333 | 2 | 1758.116667 | 10.92034 | 9.66E−05 | 3.158846 |
| Within Groups | 9176.7 | 57 | 160.9947368 | | | |
| Total | 12692.9333 | 59 | | | | |
| Total | 12692.9333 | 59 | | | | |

Table 17 compares the seed stalk spread measured in centimeters of lettuce cultivar Pro Green 76 with commercial lettuce cultivars Tehema and Bergams and shows the ANOVA results that indicate significant differences in the seed stalk spread between the varieties. Data were taken in 2011 in Bottonwillow, Calif. on 20 plants of each variety.

TABLE 17

Seed Stalk Spread (cm)

| Pro Green 76 | Tehema | Bergams Green |
|---|---|---|
| 40 | 40 | 41 |
| 50 | 45 | 40 |
| 45 | 44 | 44 |
| 44 | 44 | 45 |
| 50 | 45 | 40 |
| 52 | 40 | 41 |
| 45 | 38 | 40 |
| 40 | 40 | 38 |
| 50 | 44 | 35 |
| 40 | 40 | 40 |
| 39 | 40 | 38 |
| 40 | 44 | 35 |
| 38 | 42 | 36 |
| 40 | 40 | 37 |
| 45 | 38 | 39 |
| 50 | 35 | 40 |
| 48 | 39 | 41 |
| 45 | 42 | 42 |
| 40 | 45 | 40 |
| 45 | 35 | 35 |

Anova: Single Factor

SUMMARY

| Groups | Count | Sum | Average | Variance |
|---|---|---|---|---|
| Preogreen 76 | 20 | 886 | 44.3 | 20.22105 |
| Tehema | 20 | 820 | 41 | 9.789474 |
| Bergams Green | 20 | 787 | 39.35 | 7.818421 |

ANOVA

| Source of Variation | SS | df | MS | F | P-value | F crit |
|---|---|---|---|---|---|---|
| Between Groups | 254.1 | 2 | 127.05 | 10.07562 | 0.000179 | 3.158846 |
| Within Groups | 718.75 | 57 | 12.60964912 | | | |
| Total | 972.85 | 59 | | | | |

DEPOSIT INFORMATION

Applicants have made a deposit of at least 2500 seeds of with the American Type Culture Collection (ATCC), Manassas, Va., 20110-2209 U.S.A., ATCC Deposit No: PTA-12300. This deposit of the Lettuce Variety Pro Green 76 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Cultivar Protection Act (7 USC 2321 et seq.).

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the American Type Culture Collection, Manassas, Va.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed of lettuce cultivar Pro Green 76, wherein a representative sample of seed of said cultivar was deposited under ATCC Accession No. PTA-12300.

2. A lettuce plant, or a part thereof, produced by growing the seed of claim 1.

3. A tissue culture produced from protoplasts or cells from the plant of claim 2, wherein said cells or protoplasts are produced from a plant part selected from the group consisting of leaf, pollen, embryo, cotyledon, hypocotyl, meristematic cell root, root tip, pistil, anther, ovule, flower, shoot, stem, seed, and petiole.

4. A lettuce plant regenerated from the tissue culture of claim 3, wherein the plant has all of the morphological and physiological characteristics of cultivar Pro Green 76.

5. A method for producing a lettuce seed comprising crossing two lettuce plants and harvesting the resultant lettuce seed, wherein at least one lettuce plant is the lettuce plant of claim 2.

6. A lettuce seed produced by the method of claim 5.

7. A lettuce plant, or a part thereof, produced by growing said seed of claim 6.

8. The method of claim 5, wherein at least one of said lettuce plants is transgenic.

9. A method of producing a male sterile lettuce plant, wherein the method comprises introducing a nucleic acid molecule that confers male sterility into the lettuce plant of claim 2.

10. A male sterile lettuce plant produced by the method of claim 9.

11. A method of producing an herbicide resistant lettuce plant, wherein said method comprises introducing a gene conferring herbicide resistance into the plant of claim 2, wherein the gene is selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile.

12. An herbicide resistant lettuce plant produced by the method of claim 11.

13. A method of producing a pest or insect resistant lettuce plant, wherein said method comprises introducing a gene conferring pest or insect resistance into the plant of claim 2.

14. A pest or insect resistant lettuce plant produced by the method of claim 13.

15. The lettuce plant of claim 14, wherein the gene encodes a Bacillus thuringiensis endotoxin.

16. A method of producing a disease resistant lettuce plant, wherein said method comprises introducing a gene conferring disease resistance into the plant of claim 2.

17. A disease resistant lettuce plant produced by the method of claim 16.

18. A method of producing a lettuce plant with a value-added trait, wherein said method comprises introducing a gene conferring a value-added trait into the plant of claim 2, where said gene encodes a protein selected from the group consisting of a ferritin, a nitrate reductase, and a monellin.

19. A lettuce plant with a value-added trait produced by the method of claim 18.

20. A method of introducing a desired trait into lettuce cultivar Pro Green 76 wherein the method comprises:
   (a) crossing a Pro Green 76 plant, wherein a representative sample of seed was deposited under ATCC Accession No. PTA-12300, with a plant of another lettuce cultivar that comprises a desired trait to produce progeny plants wherein the desired trait is selected from the group consisting of male sterility, herbicide resistance, insect or pest resistance, modified bolting and resistance to bacterial disease, fungal disease or viral disease;
   (b) selecting one or more progeny plants that have the desired trait to produce selected progeny plants;
   (c) crossing the selected progeny plants with the Pro Green 76 plant to produce backcross progeny plants;
   (d) selecting for backcross progeny plants that have the desired trait and all of the physiological and morphological characteristics of lettuce cultivar Pro Green 76 listed in Table 1; and
   (e) repeating steps (c) and (d) two or more times in succession to produce selected third or higher backcross progeny plants that comprise the desired trait and all of the physiological and morphological characteristics of lettuce cultivar Pro Green 76 listed in Table 1.

21. A lettuce plant produced by the method of claim 20, wherein the plant has the desired trait.

22. The lettuce plant of claim 21, wherein the desired trait is herbicide resistance and the resistance is conferred to an herbicide selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile.

23. The lettuce plant of claim 21, wherein the desired trait is insect or pest resistance and the insect or pest resistance is conferred by a transgene encoding a Bacillus thuringiensis endotoxin.

* * * * *